United States Patent [19]

Nakaya et al.

[11] Patent Number: 4,801,835

[45] Date of Patent: Jan. 31, 1989

[54] ULTRASONIC PROBE USING PIEZOELECTRIC COMPOSITE MATERIAL

[75] Inventors: Chitose Nakaya, Tokyo; Hiroshi Takeuchi, Matsudo; Kageyoshi Katakura, Tokyo, all of Japan

[73] Assignees: Hitachi Medical Corp.; Hitachi Ltd., both of Tokyo, Japan

[21] Appl. No.: 100,238

[22] Filed: Sep. 23, 1987

[30] Foreign Application Priority Data

Oct. 6, 1986 [JP] Japan .................. 61-236141
Oct. 6, 1986 [JP] Japan .................. 61-236142
Apr. 10, 1987 [JP] Japan .................. 62-86884

[51] Int. Cl.⁴ .................................. H01L 41/08
[52] U.S. Cl. ........................... 310/358; 310/334; 310/366; 310/800
[58] Field of Search .................. 310/357–359, 310/800, 366, 334–336

[56] References Cited

U.S. PATENT DOCUMENTS 4,518,889 5/1985 Hoen ............................ 310/357
4,572,981 2/1986 Zola ............................. 310/357
4,658,176 4/1987 Nakaya ........................ 310/334
4,683,396 7/1987 Takeuchi et al. ............ 310/357 X

FOREIGN PATENT DOCUMENTS 58-022046 2/1983 Japan .
60-114239 6/1985 Japan .

Primary Examiner—Mark O. Budd
Attorney, Agent, or Firm—Antonelli, Terry & Wands

[57] ABSTRACT

In an ultrasonic probe produced by forming stripe electrodes on a piezoelectric composite material consisting of a plurality of piezoelectric ceramic rods buried in an organic material, the gaps between the stripe electrodes in the direction of disposition are expanded as much as possible while the gaps of the piezoelectric ceramic rods or their width in the direction of disposition is reduced as much as possible. When the width of the piezoelectric ceramic rod is reduced in the manner described above, the width of the piezoelectric ceramic rod is expanded in a direction orthogonal to the direction of disposition or the gaps of the piezoelectric ceramic rods in that direction is reduced in order to reduce crosstalk and to improve flexibility and sensitivity.

7 Claims, 8 Drawing Sheets $W' = W$ $W' = 0.15W$

ULTRASONIC PROBE USING PIEZOELECTRIC COMPOSITE MATERIAL

BACKGROUND OF THE INVENTION

This invention relates generally to an ultrasonic probe using a piezoelectric composite material, and more particularly to a multi-element ultrasonic probe forming a plurality of independently operable piezoelectric vibrators by disposing electrodes separately in a stripe form.

A typical known piezoelectric composite material 1 has a structure wherein a large number of piezoelectric ceramic rods such as lead zirconate titanate (hereinafter called "PZT") are arranged regularly in both X- and Y-directions with uniform spacings between them as depicted in FIG. 1 of the accompanying drawings. The structures of the principal portions of ultrasonic probes, which use such a piezoelectric composite material, are equipped with a plurality of electrodes (hereinafter called "stripe electrode elements") disposed in the stripe form on the surface of the piezoelectric composite material and enable the piezoelectric composite material at the portion corresponding to each stripe electrode to operate independently as a piezoelectric vibrator, are disclosed in Japanese Patent Laid-Open No. 220461983, U.S. patent specification No. 4,628,223. To reduce a side lobe, on the other hand, U.S. patent specification No. 4,658,176 discloses the arrangement wherein the pitch of the piezoelectric ceramic rods is smaller than the wavelength of the sonic wave of the fundamental resonance frequency and the width and pitch of the individual piezoelectric ceramic rods are sequentially different in the direction of their disposition. Incidentally, focusing mechanisms by phase adjustment of driving signals of the piezoelectric vibrators, and the like, are known in the art and hence, the description of such mechanisms is hereby omitted.

However, the prior art technique described above does not take into account the arrangement wherein the probe is constituted by use of a piezoelectric composite material having a high volume fraction for the piezoelectric ceramic rods. For, the piezoelectric composite material having a high volume fraction involves the problems that it has low flexibility because the occupying volume of organic materials that contribute to the flexibility of the piezoelectric composite material becomes small, the construction of a curved surface ultrasonic probe becomes therefore difficult, and since the occupying volume of the piezoelectric composite material is great, on the contrary, the spacing between channels becomes so small that cross-talk increases.

Japanese Patent Laid-Open No. 114239/1985 discloses a rectangular or ring-like electrode structure and U.S. patent application Ser. No. 661,928/'84 discloses an ultrasonic probe using a piezoelectric composite material whose volume fraction is from about 0.15 to about 0.75.

These prior art references do not consider, either, the drop of flexibility of the piezoelectric composite material in the same way as the prior art technique described already.

All the prior art techniques described above are merely based on the concept that when the volume fraction of the piezoelectric ceramic rod increases in the piezoelectric composite material, acoustic impedance of the piezoelectric material increases so that matching with water or a live body becomes difficult to establish. Therefore, they do not consider sufficiently a piezoelectric composite material having excellent vibration characteristics and an acoustic matching layer as the piezoelectric material for the probe.

On the other hand, U.S. patent application Ser. No. 944,523 discloses an input device using a piezoelectric composite material for computers, electronic typewriters, and the like, but this reference is different in the technical field and structure from the present invention and is therefore merely illustrative as a prior development.

SUMMARY OF THE INVENTION

It is an object of the present invention to provide an ultrasonic probe which does not lose flexibility even by use of a piezoelectric composite material whose piezoelectric ceramic rods have a volume fraction of as high as at least 0.60 and which does not either increase crosstalk between channels.

In a piezoelectric composite material consisting of piezoelectric ceramic rods disposed in a direction (X direction), in which stripe electrodes are formed, and in a direction (Y direction) orthogonal to the former, the object described above can be accomplished by a ultrasonic probe having a construction wherein there is used a piezoelectric composite material which expands the gaps 9E between the stripe electrodes (if there is any piezoelectric ceramic rod whose part projects into the gaps between the stripe electrodes, the term "gap" will hereinafter means the balance after subtraction of such a projecting portion) to such an extent that cross-talk does not become a problem, in the X direction, and minimizes the gap between the piezoelectric ceramic rods (which are covered with the stripe electrodes) in the y direction.

The object described above can be also accomplished by constituting the ultrasonic probe by use of a piezoelectric composite material having a structure wherein the width of the piezoelectric ceramic rods covered with the stripe electrodes is reduced in the X direction while the gap in the Y direction is reduced, or the width of the piezoelectric material is increased in order to increase the density of the piezoelectric material. According to the arrangement described above, the probe is flexible even when the volume fraction of the piezoelectric ceramic rods is increased, cross-talk can be reduced and the drop of sensitivity can be restricted.

Additionally, if the width of the piezoelectric material or the length of the gaps between the piezoelectric ceramic rods is uniform in both the X- and Y-directions, the production process can be simplified and high dimensional accuracy can be secured.

It is another object of the present invention to provide a structure which further increases flexibility described above, and forms grooves at part of an organic matter portion of the piezoelectric composite material having electrodes formed on one of the surfaces thereof so that the piezoelectric composite material can be deformed more easily and a curved surface ultrasonic probe having a smaller radius of curvature can be accomplished.

In the structure described above, it is still another object of the present invention to provide a structure which includes an acoustic matching layer whose acoustic impedance is between the piezoelectric composite material and the live body, as one of its constituent elements and wherein the ratio W/t between the width W and height t of the piezoelectric ceramic rod is smaller than 1 and the volume fraction of this piezoelectric ceramic rod is at least 0.35.

DESCRIPTION OF THE PREFERRED EMBODIMENTS

One embodiment of the present invention will be described with reference to FIGS. 2A and 2B.

Figure 1:
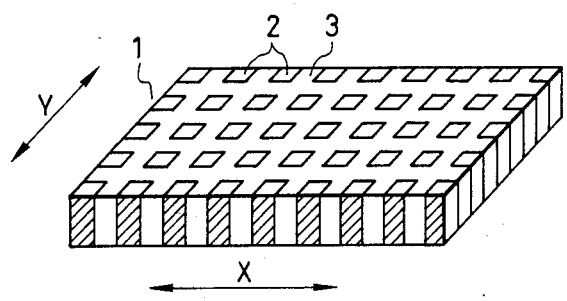
FIG. 1 is a structural view of a conventional piezoelectric composite material.
Figure 2A:
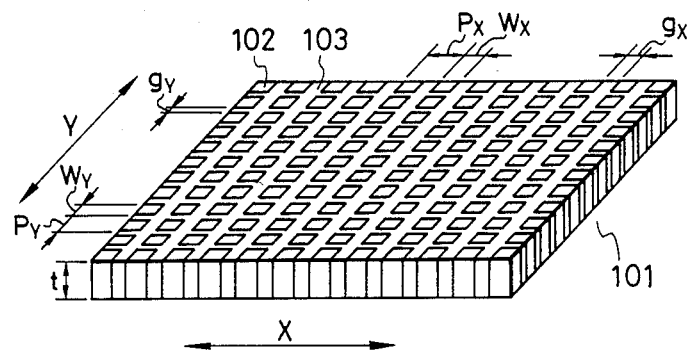
FIGS. 2A and 2B are structural explanatory views of a piezoelectric composite material and its electrodes used in one embodiment of the present invention, respectively.

FIG. 2A shows a piezoelectric composite material 101. Reference numeral 102 represents a piezoelectric ceramic rod such as PZT and 103 represents an organic material. The direction of arrangement of stripe electrodes will be called "X" and a direction orthogonal to the former, "Y". Furthermore, the pitch of arrangement of the piezoelectric ceramic rods in the X- and Y-directions will be called "Px" and "Py", respectively, the width of the piezoelectric ceramic rod and their gaps in the X- and Y-directions will be called, "Wx" and "Wy" and "gx" and "gy", respectively.

Figure 2B:
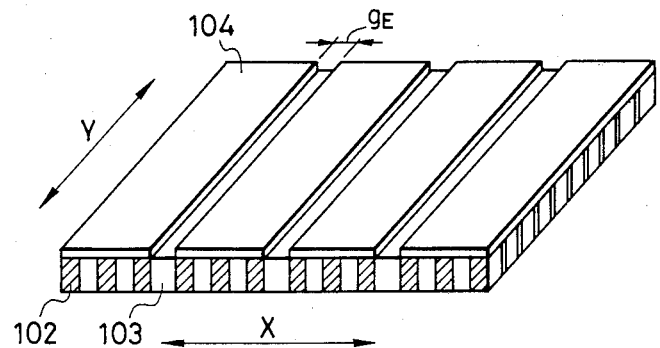

FIG. 2B shows the state where the stripe electrodes 104 are formed. Here, the relation $f(x) = Wx/Px$, $f(y) = Wy/Py$ is established where $f(x)$ is the proportion between Wx and Px of the piezoelectric ceramic rods in the X direction and $f(y)$ is the proportion between Wy and Py of the piezoelectric ceramic rods in the Y direction. The characterizing feature of the present invention resides in that at least one of the width (w) of the piezoelectric ceramic rod and the gaps gx and gy between each of the piezoelectric ceramic rods assume different values in the X and Y directions and the relations $gx \geq gy$ and $f(x) < f(y)$ exist.

In the conventional structure, P, W and g are the same in the X and Y directions when the volume fraction of the piezoelectric ceramic rods 102 ($v_l$, $1 > v_1 > 0$) in the piezoelectric composite material 101 (such as when $v_1 \geq 0.6$). In this case, the width of gx becomes inevitably small and the gap between the adjacent stripe electrodes covering the piezoelectric ceramic rod having this small gx value becomes small, too, so that cross-talk is likely to increase between the stripe electrodes and flexibility drops in the X direction. Incidentally, the volume fraction described above is given by:

$$v_1 Wx/Px \times Wy/Py$$

Figure 3A:
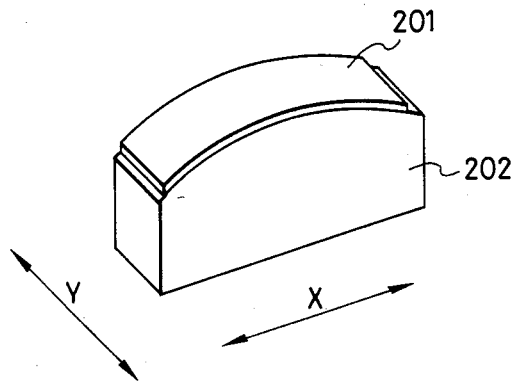
FIGS. 3A and 3B are schematic views of conventional curved surface ultrasonic probes.
Figure 3B:
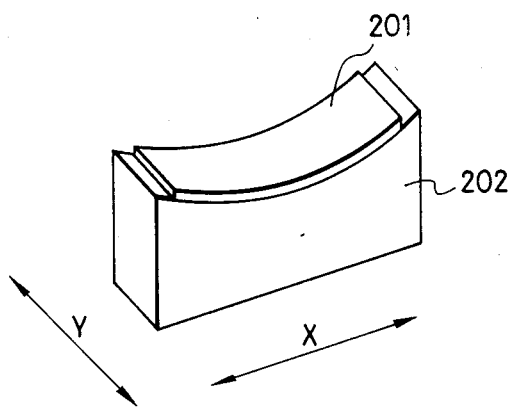

The increase in cross-talk reduces resolution and the drop in flexibility makes it difficult to form a convex array probe and a concave array probe shown in FIGS. 3A and 3B. (As to the convex array probe and its utility, refer, for example, to Japanese Journal of Medical Ultrasonics, 43-C-70, 1983, December, and the like). In FIGS. 3A and 3B, reference numeral 201 represents the piezoelectric composite material, 202 is a support bed called a "backing material" and X and Y are the direction of arrangement of the stripe electrodes and the direction orthogonal to the former, respectively, in the same way as in FIGS. 2A and 2B. In these drawings, lead wires, the acoustic matching layer and an acoustic lens are omitted for the purpose of simplification.

The gap $g_e$ between the adjacent stripe electrodes in the direction of their disposition is expanded to such an extent as not to increase cross-talk and not to lose flexibility. The problem of cross-talk does not occur if the gap is up to about 30 μm. Preferably, the relation $gx/Wx \geq 0.1$ is satisfied in order to keep flexibility. The volume fraction of the piezoelectric vibrator is given by $v_1 = f(x) \cdot f(y)$. When, for example, gx between all the piezoelectric ceramic rods is increased in order to increase the gaps between the adjacent stripe electrodes (with the proviso that wx is the same), gy may be made smaller so as to increase the density of the piezoelectric ceramic rod covered by the stripe electrodes and not to decrease sensitivity of the probe (with the proviso that Wy is the same). When the predetermined volume fraction $v_1$ is satisfied and cross-talk is reduced in the manner described above, there can be accomplished a flexible piezoelectric composite material, and a probe using such a piezoelectric composite material.

Figure 4A:
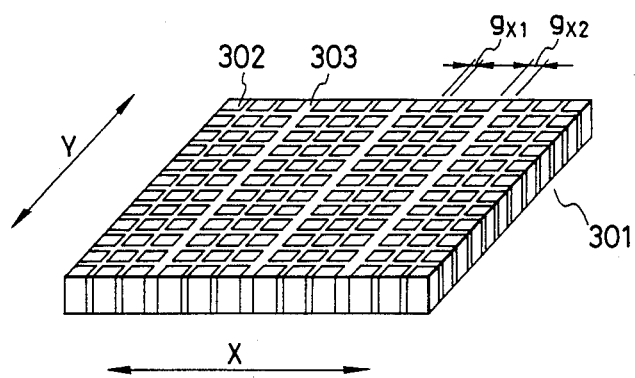
FIGS. 4A, 4B and 4C are structural explanatory views of the piezoelectric composite material and its electrodes in the embodiment of the present invention.
Figure 4B:
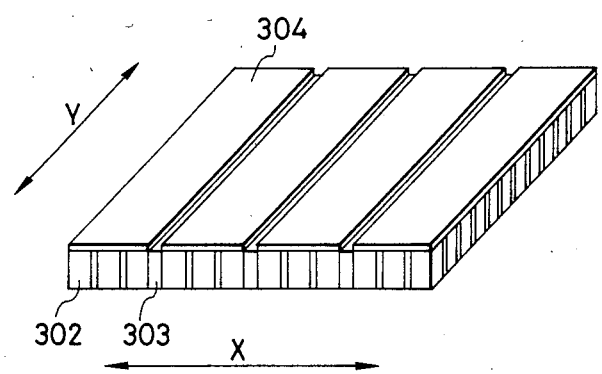
Figure 4C:
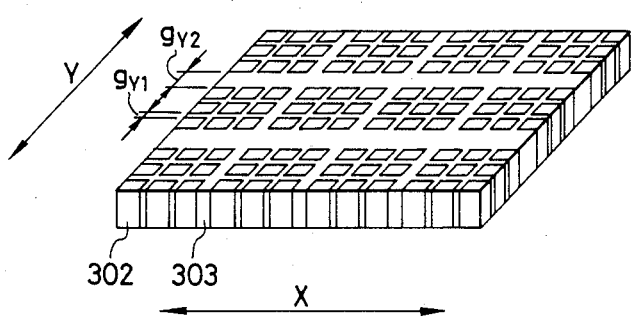

FIGS. 4A, 4B and 4C show another embodiment when the volume fraction $v_1$ is great. Reference numeral 301 represents the piezoelectric composite material, 302 is the piezoelectric ceramic rod and 303 is the organic material. The gaps in the X direction are two, i.e. $gx_1$ and $gx_2$. The latter ($gx_2$) is the gap for cutting off the stripe electrodes 304 while the former ($gx_1$) is the gap in the X direction between the adjacent piezoelectric ceramic rods existing inside the portion covered by the stripe electrodes 304. The volume fraction $v_1$ can be made great inside the electrode 304 by making gy small. Since $gx_2$ can be made great, the problems of cross-talk and flexibility do not occur. Furthermore, where a large volume fraction $v_1$ and flexibility in the Y direction are required, high flexibility can be obtained by increasing $gy_2$ while disposing two gaps $gy_1$ and $gy_2$ as shown in FIG. 4C. The case where $v_1$ is large is shown above; however, in the case where a small $v_1$ and flexibility particularly in the Y direction are required, this invention enables gy and gx to be made larger. Here, the values gx and gy represent the exclusive values containing $gx_1$, $gx_2$ and $gy_1$, $gy_2$, respectively.

Still another embodiment of the present invention will be described with reference to FIG. 5. Reference numeral 401 represents the piezoelectric composite material. A large number of piezoelectric ceramic rods 402 are buried in the organic material 403 and grooves 405a are formed to separate the stripe electrodes 404a and 404b. In accordance with the prior art technique, the electrodes 404 are formed by vacuum deposition but the width of a mask for forming the electrodes is about 50 μm and cannot be reduced any more. Moreover, due to deformation of the mask, it has been extremely difficult by vacuum deposition to form the electrodes 404 highly accurately. When, for example, the gap between the piezoelectric ceramic rods 402 is about 30 μm, the width of the mask is at least about 50 μm in accordance with the conventional mask vacuum deposition technique so that those piezoelectric ceramic rods 402 whose electrode is formed only partially occur unavoidably and reduce the performance of the piezoelectric composite material 401.

In accordance with the present invention, the gap 405 smaller than the gap between the piezoelectric ceramic rods 402 can be formed easily by cutting technique using a dicing saw and the electrodes can be separated completely.

Figure 5:
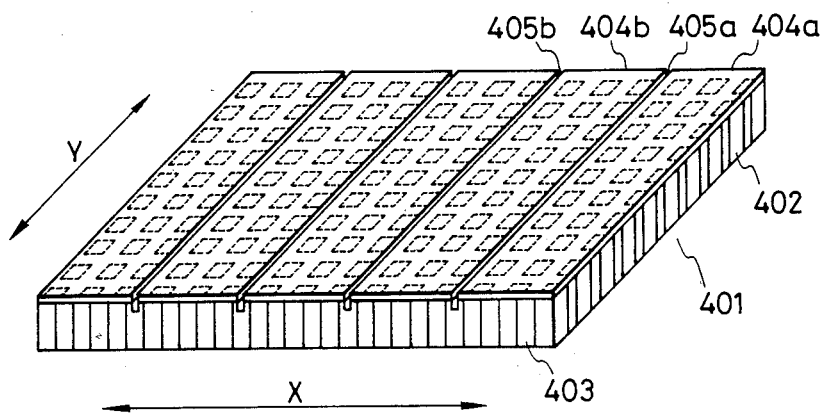
FIG. 5 is a perspective view useful for explaining the formation of stripe electrodes in one embodiment of the present invention.

Furthermore, since the groove 405 is formed, flexibility increases in the X direction in FIG. 5.

It has been desired recently that the radius of curvature of a convex array probe be further reduced. In accordance with the present invention wherein the grooves are disposed, flexibility can be improved so that the convex array probe having a smaller radius of curvature can be constituted extremely advantageously.

Figure 6A:
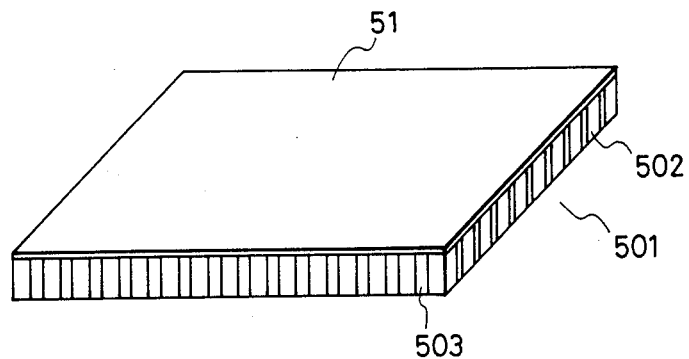
FIGS. 6A, 6B and 6C are process views showing the production method of the piezoelectric composite material having the stripe electrodes described above.
Figure 6B:
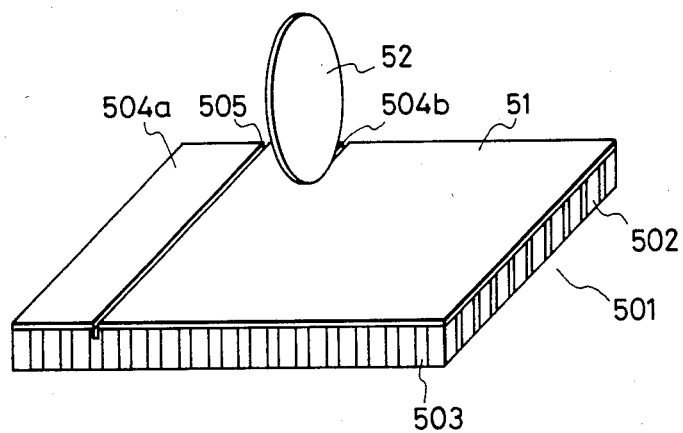
Figure 6C:
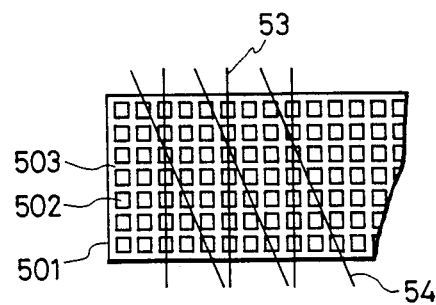

FIGS. 6A to 6C show the production method. An electrode 51 is formed on the entire surface of the piezoelectric composite material 501 as shown in FIG. 6A, and grooves 505 are then formed by a dicing saw as shown in FIG. 6B. Here, reference numeral 52 represents the blade of the dicing saw, which rotates at a high speed, forms the groove 505 in the direction crossing at right angles the X direction and at the same time, forms the stripe electrodes 504a, 504b. Since the blade from about 15 μm is available, the problem of the mask vacuum deposition described already does not occur. Furthermore, where only flexibility is required, the groove 505 need not always be formed between the piezoelectric ceramic rods but may be formed in a slanting direction with respect to the arrangement of the piezoelectric ceramic rods 502, such as the arrangement shown in FIG. 6C, for example. FIG. 6C is a top view of the piezoelectric composite material 501 and the electrodes 51 are omitted from this drawing. The cutting grooves may be formed in the direction of line 53 or 54.

Figure 7:
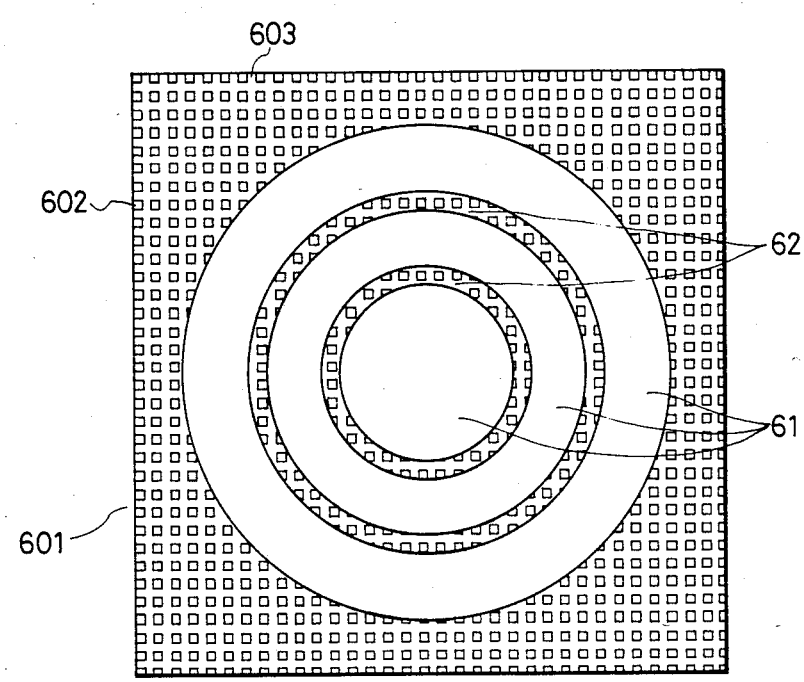
FIG. 7 is a plan view of a multi-ring electrode in one embodiment of the present invention.

FIG. 7 is a plan view when electrodes are formed in a multiple ring form. Reference numeral 61 represents the ring-like electrodes and reference numeral 62 represents the grooves between the electrodes 61. The dicing saw cannot be used in this case but the grooves can be formed by ultrasonic machining or the like after the electrode 61 (the round electrode in the case of FIG. 7) is formed on the surface of 601 in the same way as FIGS. 6A to 6C. In accordance with the ultrasonic machining technique, the width of the groove 62 becomes considerably great but flexibility can be of course increased.

The characterizing feature of the present invention resides in that the ultrasonic probe is constituted by use of the piezoelectric composite material having the electrodes with the grooves. To constitute the probe, it is necessary to bond the piezoelectric composite material to a support bed called a "backing material" and to take out lead wires, but since they can be accomplished by known means, the description will be hereby omitted.

Still another embodiment of the present invention will be described with reference to FIGS. 8A to 8C.

First of all, the piezoelectric composite material 101 to be dealt with is such as shown in FIG. 2A and is omitted from illustration. It will be hereby assumed that in the structure shown in FIG. 2A, the width of the piezoelectric ceramic rod 102 has the relation $Wx = Wy = W$ and its height, t. As described in IEICE Technical Report ED 84-157, too, various probes can be constituted by use of the piezoelectric composite material, but a single probe as a simple example of these probes is shown in FIG. 8A for ease of explanation. The electrodes 104 and 105 are formed on the upper and lower surfaces of the piezoelectric composite material 101 by vacuum deposition of Cr-Au, or the like, and lead wires 104' and 105' are connected. Furthermore, the backing material 106 is bonded and an acoustic matching layer 107 is formed. FIG. 8B shows the relation between W/t of the piezoelectric ceramic rod and its vibration state. Reference numerals 109 and 110 represent the electrodes on the upper and lower surfaces, respectively. Incidentally, PZT is used as the piezoelectric material and its vibration analysis is made by a finite element method. Reference numerals 112 to 116 represent the vibration state of the piezoelectric ceramic rod 108 in accordance with the W/t value at a time $\frac{1}{2} \cdot T$ when a square pulse 111 having a pulse width $\frac{1}{2} \cdot T$ is applied across the electrodes 109 and 110 at a time 0. Here, symbol T represents the period of the fundamental vibration in the longitudinal direction of the piezoelectric ceramic rod 108. In order to have the vibration state more easily comprehensive, displacement is expanded and the longitudinal direction is shown in 2× than the transverse direction. Furthermore, since there is symmetry, only the upper half is shown. Reference numerals 117 to 121 represent the stationary state of the piezoelectric ceramic rod 108. As can be seen from the diagram, the vibration of the piezoelectric ceramic rod tends to come close to only the longitudinal vibration with the decreasing W/t value. Only the longitudinal vibration is necessary for the probe and other vibrations such as the lateral vibration become the noise components. Therefore, the piezoelectric ceramic rod 102 in the piezoelectric composite material 101 preferably vibrates in only the longitudinal direction, and W/t is preferably smaller than 1 as can be understood from FIG. 8B. FIG. 8C shows the result of sensitivity measurement when a probe is constituted by use of the piezoelectric composite material wherein the volume fraction of the piezoelectric ceramic rod 102 is kept constant but W/t is changed (represented by characteristic curve 122). The sensitivity measurement is carried out by placing a flat sheet-like reflector inside water 30 mm distant from the probe and measuring the reflection signal from the reflector. From this diagram, too, it can be understood that sensitivity becomes high when W/t <1 and that if W/t is too small, sensitivity tends to drop. The shapes of 101 and 102 should be determined in consideration of both FIGS. 8B and 8C but relation W/t <1 is the essential condition in order to accomplish a high quality (high sensitivity and high resolution) probe by use of the piezoelectric composite material.

Figure 8A:
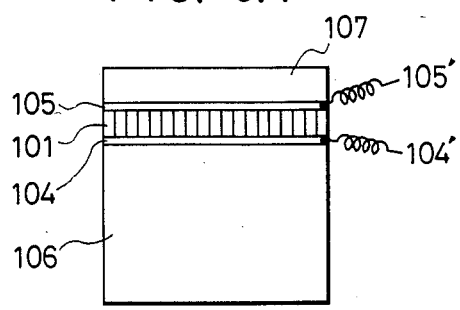
FIGS. 8B and 8C are a structural view of the ultrasonic probe useful for explaining one embodiment of the present invention, a diagram showing the result of analysis of the vibration state with respect to W/t of the piezoelectric ceramic rod and a diagram showing the sensitivity characteristics of the probe with respect to W/t of the piezoelectric ceramic rod, respectively.
Figure 9A:
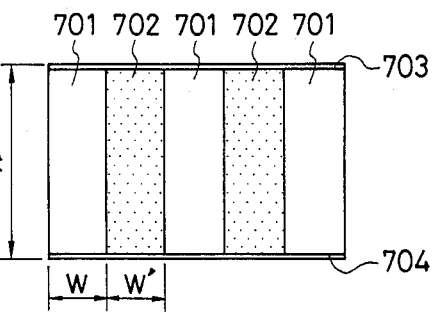
FIGS. 9A, 9B and 9C are diagrams showing the result of analysis of the vibration state of the piezoelectric ceramic rod and an organic material.
Figure 9B:
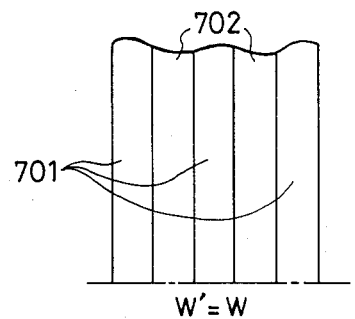
Figure 9C:
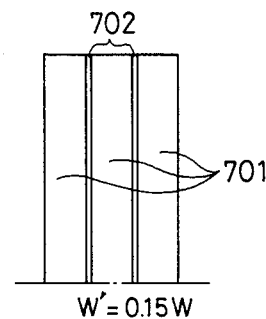

When a single probe such as shown in FIG. 8A or an electronic scanning type multi-element ultrasonic probe is constituted, sensitivity of the probe will drop or its directivity characteristics will get deteriorated if the piezoelectric ceramic rod and the organic material surrounding the former exhibit mutually opposite vibrations. It is therefore desirable that the piezoelectric ceramic rod and the organic material surrounding the former vibrate in the same vibration mode. Since the piezoelectric ceramic rods are buried in the organic material in the piezoelectric composite material as shown in FIG. 2A, a structure for accomplishing the vibration in the same vibration mode becomes necessary. FIGS. 9A, 9B and 9C show the vibration state when W/t of the piezoelectric ceramic rods 701 is kept constant value of 0.25 and the width W' of the organic material 702 between the ceramic rods is changed. Since the piezoelectric composite material for the probe is preferably flexible, flexible polyurethane is used here as the organic material. Incidentally, reference numerals 703 and 704 represent the electrodes on the upper and lower surfaces.

Figure 8B:
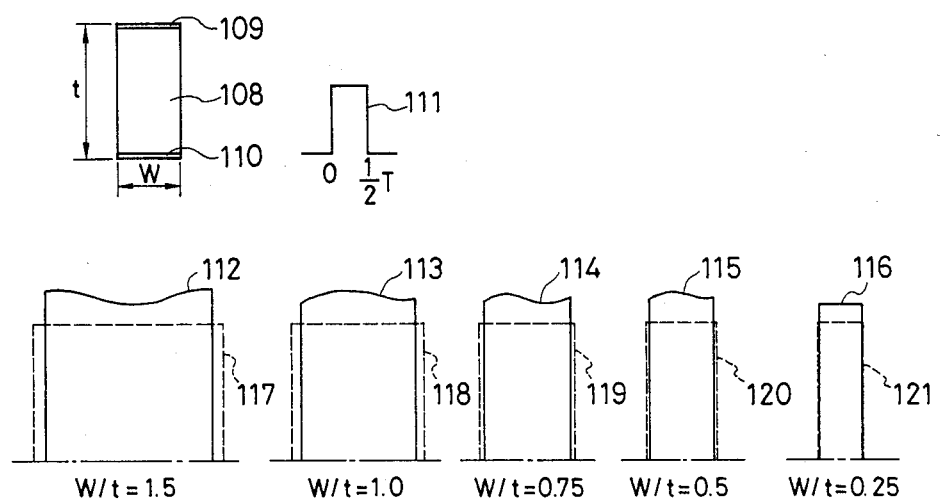
Figure 8C:
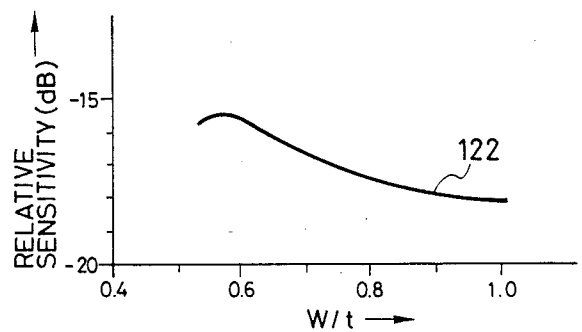

FIGS. 9B and 9C show the vibration state at the time ½·T when the electric signal is applied in the same way as in FIG. 8B. Here, symbol T represents the period of the fundamental vibration in the longitudinal direction of the piezoelectric ceramic rod 801 as described already. As can be understood from the diagram, 701 and 702 come close to the same vibration with the decreasing w' value. When W/t is constant, the small w' value means that the volume fraction ($v_1$) of the piezoelectric ceramic rod in the piezoelectric composite material is great. Therefore, it is desired for the piezoelectric composite material that $v_1$ is greater (with a smaller W/t value). Incidentally, $v_1$ corresponding to W'=W and, W'=0.15W in FIGS. 9A and 9C are 0.25 and 0.76, respectively.

Figure 10:
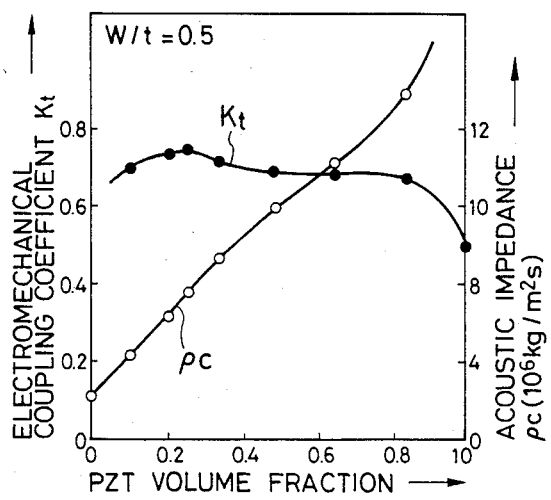
FIG. 10 is a diagram cited from a prior art reference for explaining the characteristics of the present invention.
Figure 11:
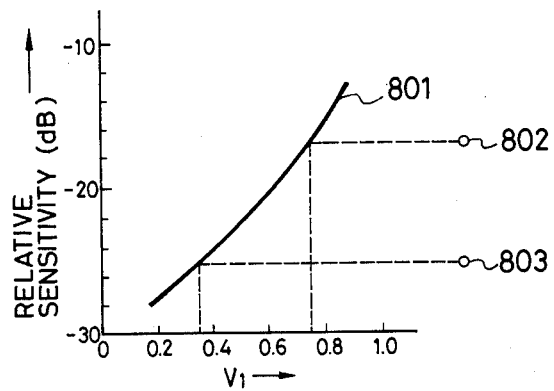
FIGS. 11, 12A, 12B and 12C are diagrams showing the sensitivity characteristics of the probe in accordance with the structure of the present invention, respectively.

As described above, the preferred properties for the piezoelectric composite material for the ultrasonic probe are that W/t of the piezoelectric ceramic rod is smaller than 1 and $v_1$ is great. However, as shown in FIG. 10 which is cited from FIG. 6 of IEICE Technical Report ED84-157, the acoustic impedance of the piezoelectric composite material (the product of the density of the material and the sonic velocity) increases with an increasing PZT volume fraction $v_1$ and matching with the live body drops. Therefore, this problem is solved by adding an acoustic matching layer. FIG. 11 shows comparatively the sensitivity of an electronic scanning type probe constructed in consideration of the factors described above. The sensitivity measurement is carried out in the same way as in FIG. 8C by use of the same transmission/reception circuit. The W/t value of the piezoelectric ceramic rod is from 0.39 to 0.75 in the piezoelectric composite material, the matching layer is a single layer, the impedance of the piezoelectric composite material using the acoustic impedance of the matching layer and the acoustic impedance of a live body are used as a geometric mean and the thickness of the matching layer is set to about ¼ wavelength of the frequency of the piezoelectric composite material. Reference numeral 801 represents the result of sensitivity measurement. Here, the sensitivity measurement is made by setting the element width of the probe to about 0.6 mm and the pitch of the piezoelectric composite material to about 0.2 mm. The sensitivity measurement is made of the conventional probe using PZT as the reference of comparison. However, this conventional probe is equipped with two matching layers and sensitivity becomes generally higher by 2 to 3 dB than that of the single matching layer. Here, PZT of the same material is used for the piezoelectric ceramic rod of the piezoelectric composite material and for the conventional probe. Reference numerals 802 and 803 represent the cases of the conventional probe where an acoustic lens is not attached and where it is attached, respectively.

In the electronic scanning type probe, the beam in the direction orthogonal to the scanning direction of the ultrasonic beam must be converged in order to improve picture quality, but in the case of the conventional probe using PZT, an acoustic lens becomes necessary because PZT is not flexible. The acoustic lens damps greatly the ultrasonic wave and in the case of 5 MHz as in this example, sensitivity of about 9 dB is brought forth. However, the acoustic lens is indispensable in order to improve the picture quality. On the other hand, the piezoelectric composite material used in this embodiment is flexible and can be shaped in a desired form. Accordingly, a good picture can be obtained by shaping each element in a concave form without using the acoustic lens. As can be understood from 801, the higher the $v_1$ value, the higher sensitivity. Sensitivity above the line 802 can be obtained when $v_1 > 0.75$ and sensitivity above the line 803 can be obtained when $v_1 > 0.35$.

Figure 12A:
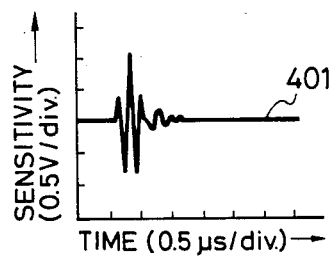
Figure 12B:
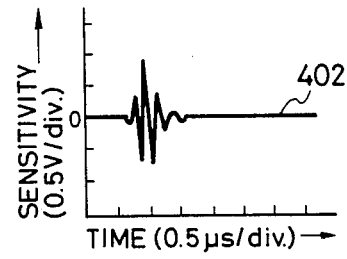
Figure 12C:
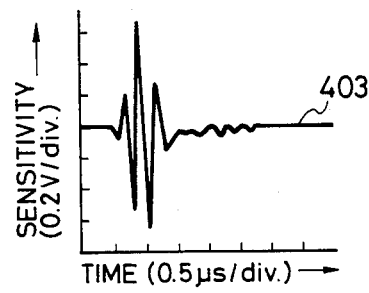

FIGS. 12A, 12B and 12C show the reception signals 401, 402 of the piezoelectric composite material probe in accordance with the structure of the present invention. Reference numerals 401 and 402 represent the cases where $v_1$ is 0.80 and 0.63, respectively. For comparison, the reception signal of the conventional PZT probe (without the acoustic lens) is represented by reference numeral 403. In comparison with 403, the reception signals 401 and 402 become short pulse (that is, high resolution) with higher sensitivity than 403 and a high performance probe can be accomplished.

As can be understood from the description given above, the present invention can reduce cross-talk between channels without losing flexibility and can easily accomplish a high performance ultrasonic probe even when a piezoelectric composite material having a high volume fraction is used.

What is claimed is:

1. An ultrasonic probe using a piezoelectric composite material having stripe electrodes arranged on at least one of an upper and lower surface thereof and with a gap between adjacent stripe electrodes, said piezoelectric composite material comprising a plurality of piezoelectric ceramic rods and an organic material having said piezoelectric ceramic rods embedded therein, wherein said piezoelectric composite material is constructed so that a relation between gx and gy and a relation between f(x) and f(y) are as follows:

$$gx \geq gy \text{ and } f(x) < f(y)$$

where

Wx: width of each piezoelectric ceramic rod in an direction which is defined as the direction of arrangement of said stripe electrodes.

gx: gap between adjacent piezoelectric ceramic rods arranged in the x-direction, $P_x = (W_x + g_x)$: pitch of said piezoelectric ceramic arranged rods in the x-direction, $f(x) \equiv W_x/P_x$ $W_y$: width of each piezoelectric ceramic rod in a y direction which is defined as the direction orthogonal to the direction of arrangement of said stripe electrodes, $g_y$: gap between adjacent piezoelectric ceramic rods arranged in the y-direction, $P_y = (W_y + g_y)$: pitch of said piezoelectric ceramic rods arrange din the y-direction, $f(y) \equiv W_y/P_y$.

2. An ultrasonic probe using a piezoelectric composite material according to claim 1, wherein said gap between adjacent stripe electrodes is greater than said gap between adjacent piezoelectric ceramic rods arranged in the x-direction.

3. An ultrasonic probe using a piezoelectric composite material according to claim 1, wherein the acoustic impedance of an acoustic matching layer disposed on said stripe electrodes is between the acoustic impedance of said piezoelectric composite material and the acoustic impedance of a live body as an object of measurement, the ratio W/t of the width W to the height t of said piezoelectric ceramic rod is smaller than 1 and the volume fraction of said piezoelectric ceramic rod of said piezoelectric composite material is at least 0.35.

4. An ultrasonic probe using a piezoelectric composite material according to claim 3, wherein the acoustic impedance is a geometric mean of the acoustic impedance of said piezoelectric composite material and the acoustic impedance of a live body and the thickness of said acoustic matching layer is a ¼ wavelength value of the longitudinal vibration frequency of said piezoelectric composite material.

5. An ultrasonic probe using a piezoelectric composite material according to claim 1, wherein grooves are formed on the surface of the organic material disposed close to the gaps between the adjacent stripe electrodes disposed on said piezoelectric composite material.

6. An ultrasonic probe using a piezoelectric composite material according to claim 2, wherein the acoustic impedance of an acoustic matching layer disposed on said stripe electrodes is between the acoustic impedance of said piezoelectric composite material and the acoustic impedance of a live body as the object of measurement, the ratio W/t of the width W of said piezoelectric ceramic rod to its height t is smaller than 1 and the volume fraction of said piezoelectric ceramic rod of said piezoelectric composite material is at least 0.35.

7. An ultrasonic probe using a piezoelectric composite material according to claim 2, wherein grooves are formed on the surface of the organic material positioned below the gaps between adjacent stripe electrodes disposed on said piezoelectric composite material.

* * * * *